(12) United States Patent
Misu

(10) Patent No.: US 7,802,479 B2
(45) Date of Patent: Sep. 28, 2010

(54) STIRRING APPARATUS, ABNORMALITY DETERMINING METHOD OF SAME, AND ANALYZER

(75) Inventor: Takahiro Misu, Mishima (JP)

(73) Assignee: Beckman Coulter, Inc., Brea, CA (US)

( * ) Notice: Subject to any disclaimer, the term of this patent is extended or adjusted under 35 U.S.C. 154(b) by 122 days.

(21) Appl. No.: 12/351,285

(22) Filed: Jan. 9, 2009

(65) Prior Publication Data

US 2009/0120188 A1 May 14, 2009

Related U.S. Application Data

(63) Continuation of application No. PCT/JP2007/063388, filed on Jul. 4, 2007.

(30) Foreign Application Priority Data

Jul. 10, 2006 (JP) ............................ 2006-189565

(51) Int. Cl.
*G01N 29/02* (2006.01)
(52) U.S. Cl. ...................... 73/590; 73/40.5 A; 73/592; 73/600; 73/602
(58) Field of Classification Search ................ 73/12.01, 73/40.5 A, 40.5 R, 579, 590, 592, 600, 602
See application file for complete search history.

(56) References Cited

U.S. PATENT DOCUMENTS 4,960,079 A * 10/1990 Marziale et al. .......... 122/504.2
5,319,972 A * 6/1994 Oblak et al. ............... 73/290 R
6,815,216 B2 * 11/2004 Sandra et al. ............... 436/178
2007/0002678 A1    1/2007 Murakami
2009/0013763 A1 *  1/2009 Gayle ....................... 73/40.5 A
2009/0113998 A1 *  5/2009 Misu ......................... 73/61.76

FOREIGN PATENT DOCUMENTS

| JP | 62-192158 | 8/1987 |
| JP | 2000-175926 | 6/2000 |
| JP | 2001-124784 | 5/2001 |
| JP | 2001-188070 | 7/2001 |
| JP | 2005-257406 | 9/2005 |
| JP | 02008020197 A * | 1/2010 |

* cited by examiner

*Primary Examiner*—J M Saint Surin
(74) *Attorney, Agent, or Firm*—Townsend and Townsend and Crew, LLP

(57) ABSTRACT

A stirring apparatus includes an acoustic wave generating unit that is provided in a vessel keeping a liquid and generates an acoustic wave toward the liquid, the liquid being stirred by the acoustic wave; a driving unit that drives the acoustic wave generating unit; a detecting unit that detects a reflected power reflected from the acoustic wave generating unit; and a determining unit that determines a presence of an abnormality based on the reflected power detected by the detecting unit. The determining unit determines the presence of the abnormality when a difference between an in-operation reflected power which is reflected from, during an operation, the acoustic wave generating unit and a reference reflected power of the acoustic wave generating unit at a same driving frequency exceeds a predetermined value.

5 Claims, 4 Drawing Sheets

US 7,802,479 B2

STIRRING APPARATUS, ABNORMALITY DETERMINING METHOD OF SAME, AND ANALYZER

CROSS-REFERENCE TO RELATED APPLICATIONS

This application is a continuation of PCT international application Ser. No. PCT/JP2007/063388 filed on Jul. 4, 2007 which designates the United States, incorporated herein by reference, and which claims the benefit of priority from Japanese Patent Application No. 2006-189565, filed on Jul. 10, 2006, incorporated herein by reference.

BACKGROUND OF THE INVENTION

1. Field of the Invention

The present invention relates to a stirring apparatus, an abnormality determining method of the same, and an analyzer.

2. Description of the Related Art

Conventionally, as a stirring apparatus used in an analyzer, a stirring apparatus which, to avoid what is called a sample carry-over, uses a surface acoustic wave element to perform a noncontact stirring with respect to a liquid kept in a vessel has been known, for example in Japanese Patent Application Laid-Open No. 2005-257406. This stirring apparatus feeds a power having a resonance frequency and drives the surface acoustic wave element to stir the liquid kept in the vessel.

SUMMARY OF THE INVENTION

A stirring apparatus according to an aspect of the present invention includes an acoustic wave generating unit that is provided in a vessel keeping a liquid and generates an acoustic wave toward the liquid, the liquid being stirred by the acoustic wave; a driving unit that drives the acoustic wave generating unit; a detecting unit that detects a reflected power reflected from the acoustic wave generating unit; and a determining unit that determines a presence of an abnormality based on the reflected power detected by the detecting unit. The determining unit determines the presence of the abnormality when a difference between an in-operation reflected power which is reflected from, during an operation, the acoustic wave generating unit and a reference reflected power of the acoustic wave generating unit at a same driving frequency exceeds a predetermined value.

An abnormality determining method according to another aspect of the present invention is for a stirring apparatus which includes an acoustic wave generating unit that is provided in a vessel keeping a liquid and generates an acoustic wave toward the liquid, and a driving unit that drives the acoustic wave generating unit, and stirs the liquid by the acoustic wave. The abnormality determining method includes detecting an initial frequency characteristic of a reference reflected power of the acoustic wave generating unit; detecting an in-operation reflected power reflected from, during an operation, the acoustic wave generating unit; and calculating a difference between the in-operation reflected power and the reference reflected power at a same driving frequency, and determining a presence of an abnormality when the difference exceeds a predetermined value.

An analyzer according to still another aspect of the present invention stirs a plurality of different liquids to cause a reaction and analyzes a reaction liquid. The analyzer analyzes the reaction liquid by using the stirring apparatus to stir and react the plurality of different liquids.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

The inventor of the present invention has been dedicated to studying characteristics of a surface acoustic wave element. A result of the study is as follows. A surface acoustic wave element causes a reflection phenomenon in which a part of power is reflected to a power source due to an inconsistency of a circuit constant in an electric circuit. The reflected power generated by this reflection phenomenon has frequency characteristics of becoming the smallest when a driving frequency of the surface acoustic wave element is at a resonance frequency and becoming larger as the driving frequency gets away from the resonance frequency.

Meanwhile, the surface acoustic wave element, when used in a stirring apparatus, is bonded to a wall surface of a vessel, for example a cuvette, by an adhesive agent serving as an acoustic matching layer. The surface acoustic wave element normally causes a self-heating as being driven and a calorific value depends on the power to be applied and a driving frequency. On this occasion, when there is no change in physical characteristics including a bonding condition of the surface acoustic wave element to the wall surface of the cuvette and an amount of the liquid kept in the cuvette, there is no major change in a thermal conductivity through the adhesive agent and the wall surface in the stirring apparatus. Therefore, an in-operation reflected power at the time when the surface acoustic wave element causes the self-heating as being driven changes with initial frequency characteristics of a reference reflected power before the self-heating retained, and a temperature change of the surface acoustic wave element falls within a certain range.

However, when an abnormality such as a detachment of the surface acoustic wave element from the vessel and an absence of the liquid in the cuvette is present, a transmission of energy of an acoustic wave generated by the operation of the surface acoustic wave element to the cuvette and to the liquid is blocked in the stirring apparatus. Thus, the surface acoustic wave element itself overheats due to the block of the energy transmission and the reflected power at the same driving frequency changes to be larger in the stirring apparatus. Consequently, the fact is found out that as long as the stirring apparatus measures initial frequency characteristics of the reference reflected power before the self-heating in advance and compares the reference reflected power and the in-operation reflected power at the same driving frequency, a presence of the abnormality in the surface acoustic wave element can be determined.

Figure 1:
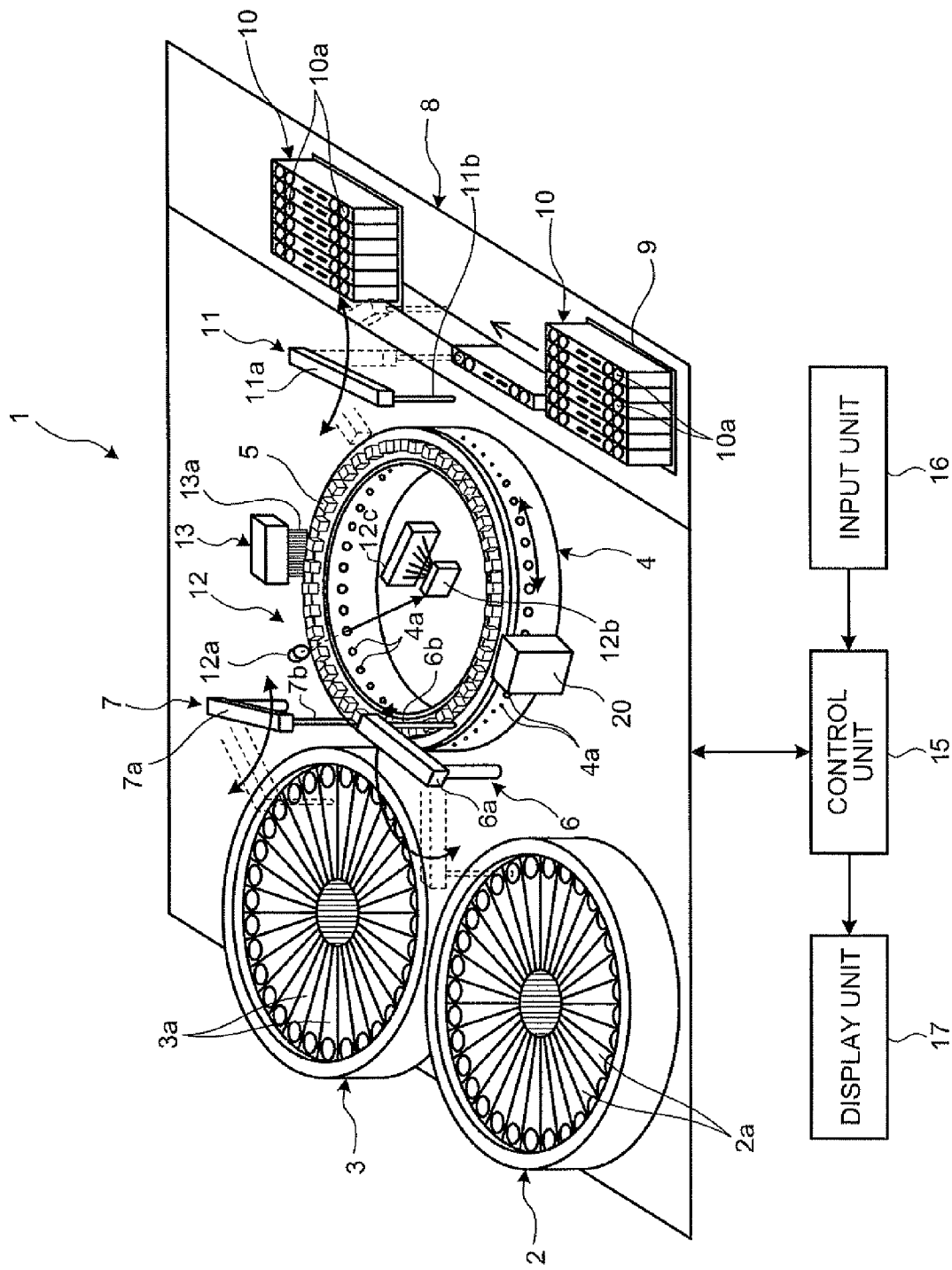
FIG. 1 is a schematic diagram of a structure of an automatic analyzer according to a first embodiment which uses a stirring apparatus of the present invention.
Figure 2:
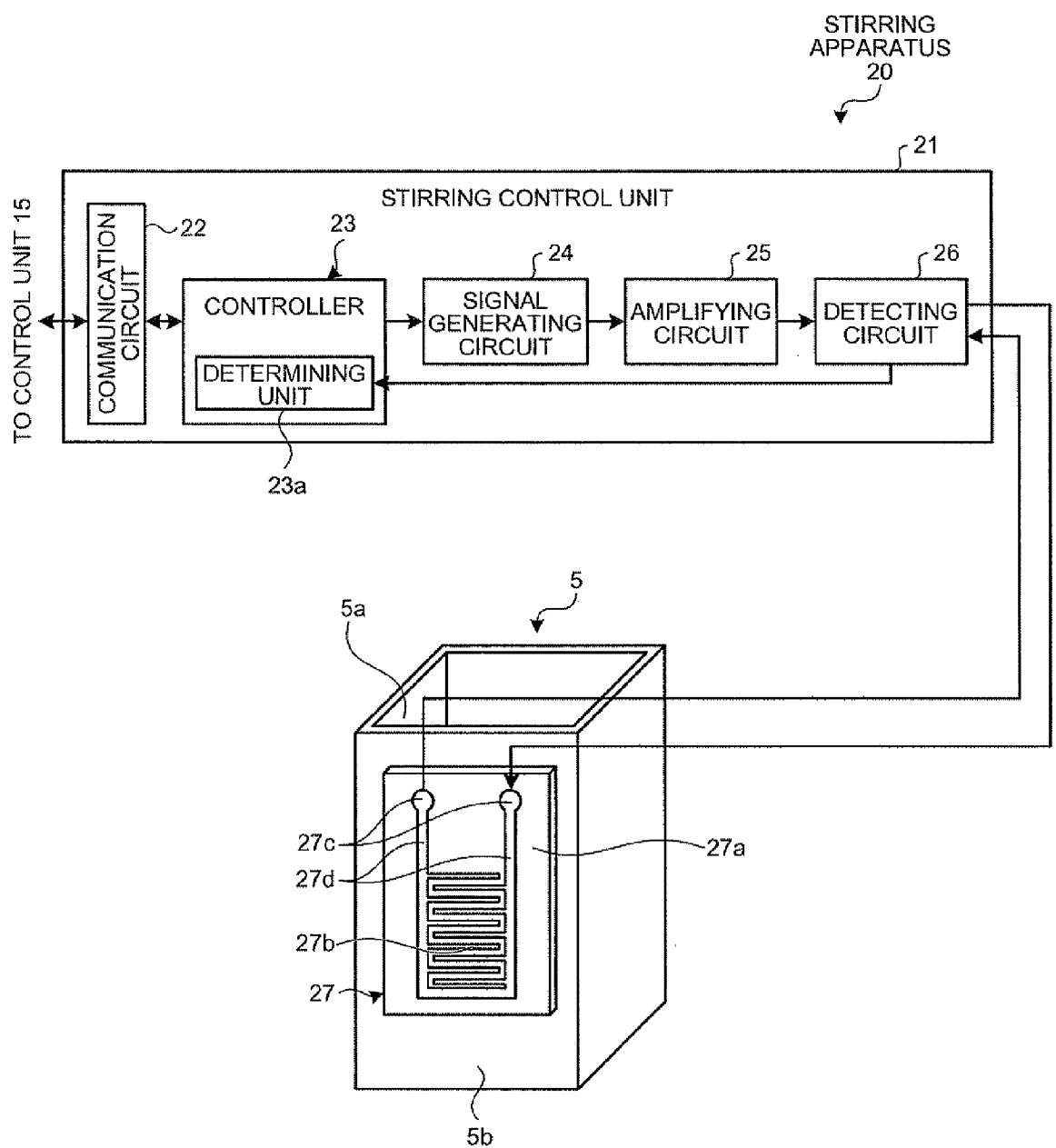
FIG. 2 is a block diagram showing a schematic structure of the stirring apparatus used in the automatic analyzer shown in FIG. 1 and a perspective view of a reaction vessel.
Figure 3:
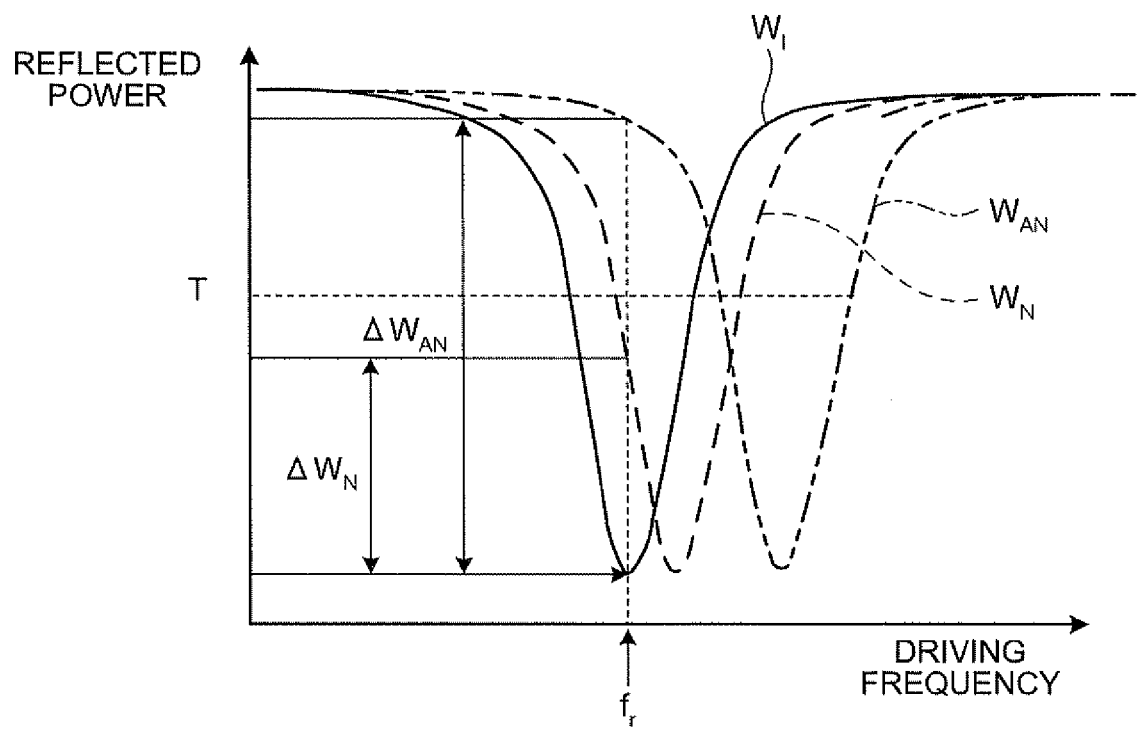
FIG. 3 shows frequency characteristics of a reference reflected power, an in-operation reflected power in a normal case, and an in-operation reflected power in an abnormal case of a surface acoustic wave element attached to the reaction vessel.
Figure 4:
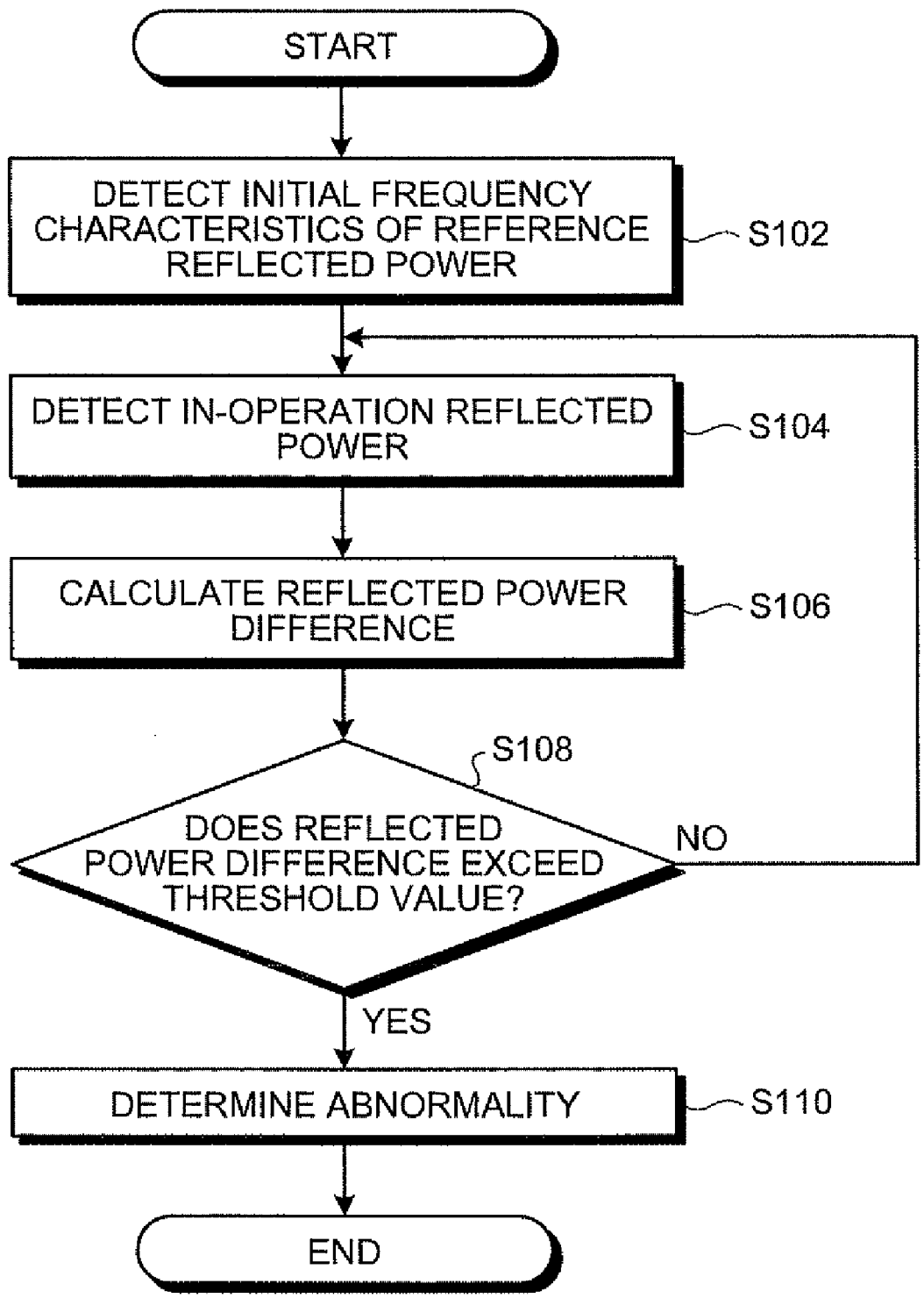
FIG. 4 is a flowchart showing a series of steps of an abnormality determination performed by a stirring control unit of the stirring apparatus.

Exemplary embodiments of a stirring apparatus, an abnormity determining method of the same, and an analyzer according to the present invention will be explained in detail below with reference to the accompanying drawings. FIG. 1 is a schematic diagram of a structure of an automatic analyzer according to a first embodiment which performs an analysis by using a stirring apparatus of the present invention. FIG. 2 is a block diagram showing a schematic structure of the stirring apparatus used in the automatic analyzer shown in FIG. 1 and a perspective view of a reaction vessel. FIG. 3 shows frequency characteristics of a reference reflected power, an in-operation reflected power in a normal case, and an in-operation reflected power in an abnormal case of a surface acoustic wave element attached to the reaction vessel.

An automatic analyzer 1 includes reagent tables 2 and 3, a cuvette wheel 4, a specimen vessel transporting mechanism 8, an analyzing optical system 12, a cleansing mechanism 13, a control unit 15, and a stirring apparatus 20 as shown in FIG. 1.

As shown in FIG. 1, the reagent tables 2 and 3 respectively have a plurality of reagent vessels 2a and 3a arranged in a circumferential direction, and carry the reagent vessels 2a and 3a in the circumferential direction by being rotated by a driving unit. On this occasion, the reagent vessels 2a each of which holds a first reagent are arranged in the reagent table 2 and the reagent vessels 3a each of which holds a second reagent are arranged in the reagent table 3.

In the cuvette wheel 4 as shown in FIG. 1, a plurality of holders which arrange the reaction vessels 5 along a circumferential direction are formed in the circumferential direction and rotated by a driving unit, which is not shown, in a direction shown by an arrow to carry the reaction vessels 5. In the cuvette wheel 4, photometry holes 4a facing in pairs in a radius direction are formed at a position corresponding to a bottom part of each holder and arranged along the circumferential direction at the same intervals with the holders. A reagent is dispensed into the reaction vessel 5 from each of the reagent vessels 2a and 3a of the reagent tables 2 and 3 respectively by reagent dispensing mechanisms 6 and 7 which are provided in the vicinity of the reaction vessel 5. The cuvette wheel 4 turns around in a counterclockwise direction by (one lap—one cuvette)/4 in one cycle and reaches a position clockwise by one reaction vessel 5 from an original position in four cycles.

The reaction vessel 5 is a vessel which, in a quadrangular hollow prism shape, has a liquid retainer 5a formed of a material, for example a glass including a heat-resistant glass and a synthetic resin such as a cyclic olefin and a polystyrene, which allows a transmission of 80% or more of a light of an analyzing light (340 nm to 800 nm) emitted from the analyzing optical system 12. In the reaction vessel 5, a surface acoustic wave element 27 (see FIG. 2) which is attached onto a side wall 5b via an adhesive agent and the like serving as an acoustic matching layer is driven by the stirring apparatus 20.

The reagent dispensing mechanisms 6 and 7 are provided with probes 6b and 7b for dispensing reagents in arms 6a and 7a which turn in the horizontal plane in directions shown by arrows respectively, and provided with cleansing units which clean the probes 6b and 7b respectively with cleansing water.

The specimen vessel transporting mechanism 8 is a transporting mechanism which transports a plurality of racks 10 arranged in a feeder 9 one by one along a direction shown by an arrow as shown in FIG. 1, and moves the rack 10 forward to perform the transportation. The rack 10 holds a plurality of specimen vessels 10a each storing a specimen. Here, whenever the moving of the rack 10 transported by the specimen vessel transporting mechanism 8 stops, the specimen in the specimen vessel 10a is dispensed into each reaction vessel 5 by a specimen dispensing mechanism 11 having an arm ha which turns around in the horizontal direction and a probe 11b. Therefore, the specimen dispensing mechanism 11 includes a cleansing unit which cleans the probe 11b with cleansing water.

The analyzing optical system 12 emits an analyzing light (340 nm to 800 nm) for analyzing a liquid sample in the reaction vessel 5 in which the reagent and the specimen are reacted, and includes a light emitting part 12a, a spectroscopic part 12b, and a light receiving part 12c as shown in FIG. 1. The analyzing light emitted from the light emitting part 12a passes through the liquid sample in the reaction vessel 5 and received by the light receiving part 12c provided at a position facing the spectroscopic part 12b. The light receiving part 12c is connected to the control unit 15.

By repeatedly pouring and absorbing a cleansing liquid and the like such as a detergent and cleansing water through a nozzle 13a after absorbing and discharging the liquid sample in the reaction vessel 5 through the nozzle 13a, the cleansing mechanism 13 cleans the reaction vessel 5 which has undergone the analysis performed by the analyzing optical system 12.

The control unit 15 serves as a part which controls an operation of each unit in the automatic analyzer 1 and analyzes a constituent concentration and the like of the specimen based on an absorbance of the liquid sample in the reaction vessel 5 based on an amount of the light emitted by the light emitting part 12a and an amount of the light received by the receiving part 12c, and a microcomputer and the like are used for example. The control unit 15 is connected to the input unit 16 such as a keyboard and to the display unit 17 such as a display panel as shown in FIG. 1.

The input unit 16 serves as a part which performs an operation of inputting a test item and the like to the control unit 15, and a keyboard and a mouse are used for example. The input unit 16 is also used for an operation of switching a frequency of a driving signal input to the surface acoustic wave element 27 of the stirring apparatus 20. The display unit 17 displays an analysis content, an alarm, and the like and a display panel is used for example.

The stirring apparatus 20 includes a stirring control unit 21 and the surface acoustic wave element 27 as shown in FIG. 2, and an operation of the surface acoustic wave element 27 is controlled by the stirring control unit 21. The stirring control unit 21 changes a frequency of a driving signal to be output to the surface acoustic wave element 27 based on information, such as a test item, a property, and an amount of the liquid sample, input from the input unit 16 via the control unit 15, and includes a communication circuit 22, a controller 23, a signal generating circuit 24, an amplifying circuit 25, and a detecting circuit 26.

The communication circuit 22 transfers a control signal with the control unit 15 and transfers data and the like by connecting the automatic analyzer 1 to an implementer's host computer via an online network.

The controller 23 uses a computerized controller (CPU) with built-in memory and timer, and includes a determining unit 23a which determines a presence of an abnormality such as a detachment of the surface acoustic wave element 27 from the reaction vessel 5 and an absence of the liquid sample in the reaction vessel 5 based on a reference reflected power before a self-heating and an in-operation reflected power. The controller 23 controls operations of the communication circuit 22, the signal generating circuit 24, the amplifying circuit 25, and the detecting circuit 26. On this occasion, the controller 23 controls a voltage and an electric current of the driving signal to be output by the signal generating circuit 24 to the surface acoustic wave element 27. By controlling the operation of the signal generating circuit 24, the controller 23 controls characteristics (a frequency, an intensity, a phase, and a wave property), waveforms (a sine wave, a triangular wave, a square wave, a burst wave, and the like), and modulations (an amplitude modulation and a frequency modulation) of an acoustic wave generated by the surface acoustic wave element 27, for example. Besides, the controller 23 can change a frequency of a high-frequency signal oscillated by the signal generating circuit 24 according to the built-in timer.

The signal generating circuit 24 has an oscillating circuit whose oscillation frequency can be changed based on the control signal input from the controller 23, generates a signal of 100 MHz to 160 MHz, divides the signal into half, and outputs a driving signal of 50 MHz to 80 MHz to the surface acoustic wave element 27. Together with the signal generating circuit 24, the amplifying circuit 25 constitutes the driving unit which drives the surface acoustic wave element 27 and amplifies, by a predetermined gain, the driving signal to be output from the signal generating circuit 24 to the surface acoustic wave element 27.

The detecting circuit 26 has a coupler; a detector which detects a power of the driving signal output after being amplified by the amplifying circuit 25 and outputs to the determining unit 23a as power data; and a detector which detects a power reflected from a transducer 27b of the surface acoustic wave element 27 and outputs to the determining unit 23a as reflected power data. The power data and the reflected power data output from the detecting circuit 26 in this manner are stored in the determining unit 23a.

In the surface acoustic wave element 27, the transducer 27b constituted by a comb-shaped electrode (an interdigital transducer) is formed on a surface of a piezoelectric substrate 27a as shown in FIG. 2. The transducer 27b serves as a sound producing part which converts the driving signal input from the stirring control unit 21 into a surface acoustic wave (acoustic wave), and a plurality of fingers constituting the transducer 27b are arranged along a longitudinal direction of the piezoelectric substrate 27a. Besides, the surface acoustic wave element 27 is connected to the stirring control unit 21 via a pair of input terminals 27c. The transducer 27b is connected to the input terminals 27c via a bus bar 27d. The surface acoustic wave element 27 is attached to the side wall 5b of the reaction vessel 5 with an intervention of an acoustic matching layer such as an epoxy resin.

In the automatic analyzer 1 constituted in the way described above, the reagent dispensing mechanisms 6 and 7 sequentially dispense the reagents from the reagent vessels 2a and 3a into the plurality of reaction vessels 5 conveyed by the rotating cuvette wheel 4 along the circumferential direction. Then, whenever the cuvette wheel 4 stops, a driving signal is output from the stirring control unit 21 via the pair of input terminals 27c. Therefore, the dispensed reagent and the specimen are sequentially stirred by the stirring apparatus 20 and reacted in the reaction vessel 5. In the automatic analyzer 1, an amount of the specimen is normally smaller than that of the reagent and the smaller amount of specimen dispensed into the reaction vessel 5 is mixed into the larger amount of reagent due to a series of flow generated in the liquid by the stirring, so that the reaction between the specimen and the reagent is accelerated.

The reaction liquid generated through the reaction between the specimen and the reagent in this manner goes through the analyzing optical system 12 when the cuvette wheel 4 starts turning around again, and the beam emitted from the light emitting part 12a passes through the reaction liquid. On this occasion, the reaction liquid of the reagent and the specimen in the reaction vessel 5 is subjected to a photometry by the light receiving part 12c and the constituent concentration and the like are analyzed by the control unit 15. The reaction vessel 5 which has undergone the analysis is cleaned by the cleansing mechanism 13 and then used for the analysis of another specimen again.

On this occasion, the determining unit 23a determines a presence of an abnormality such as a detachment of the surface acoustic wave element 27 from the reaction vessel 5 and an absence of the liquid sample in the reaction vessel 5 in the stirring apparatus 20. In other words, the surface acoustic wave element 27 causes a reflection phenomenon in which a part of the applied power is reflected by the transducer 27b and returns to the stirring control unit 21 due to an inconsistency of a circuit constant in an electric circuit. This reflection phenomenon generates a reference reflected power WI, which has frequency characteristics of becoming the smallest when the driving frequency of the surface acoustic wave element 27 is at a resonance frequency fr and becoming larger as the driving frequency gets away from the resonance frequency fr as shown by a solid line in FIG. 3.

Meanwhile, the surface acoustic wave element 27 normally causes a self-heating with its operation and a calorific value depends on the power to be applied and the driving frequency. On this occasion, when there is no change in physical characteristics including a bonding condition of the surface acoustic wave element 27 to the side wall 5b of the reaction vessel 5 and an amount of the liquid sample kept in the reaction vessel 5, there is no major change in a thermal conductivity through the adhesive agent and the side wall 5b in the stirring apparatus 20. Therefore, an in-operation reflected power WN at the time when the surface acoustic wave element 27 causes the self-heating in a normal state changes with initial frequency characteristics of the reference reflected power WI before the self-heating retained, and a temperature change of the surface acoustic wave element 27 falls within a certain range.

However, when an abnormality such as a detachment of the surface acoustic wave element 27 from the reaction vessel 5 and an absence of the liquid sample in the reaction vessel 5 is present, a transmission of an energy of an acoustic wave generated by the operation of the surface acoustic wave element 27 to the reaction vessel 5 and to the liquid sample is blocked in the stirring apparatus 20. Thus, the surface acoustic wave element 27 overheats due to the block of the energy transmission. An in-operation reflected power WAN in an abnormal case having this overheat changes to be larger than the in-operation reflected power WN at the resonance frequency fr as shown by an alternate long and two short dashes line in FIG. 3. Consequently, as long as the stirring apparatus 20 measures initial frequency characteristics of the reference reflected power WI before the self-heating in advance, stores the characteristics in the controller 23, and compares the in-operation reflected power and the reference reflected power WI at the same driving frequency by calculating their difference by the determining unit 23a, a presence of an abnormality in the surface acoustic wave element 27 can be determined.

On this occasion, a difference $\Delta$WN between the in-operation reflected power WN and the reference reflected power WI is smaller than a difference $\Delta$WAN between the in-operation reflected power WAN and the reference reflected power WI shown by the alternate long and two short dashes line at the resonance frequency fr of the surface acoustic wave element 27 as shown in FIG. 3. Therefore, a threshold value T is determined in advance with respect to the difference between the in-operation reflected power measured in the operation of the surface acoustic wave element 27 and the reference reflected power WI thereof at the same driving frequency, and stored in the determining unit 23a in the stirring apparatus 20 according to the present invention. When the difference between the in-operation reflected power and the reference reflected power WI at the same driving frequency exceeds the threshold value T, the determining unit 23a determines that an abnormality such as a detachment of the surface acoustic wave element 27 from the reaction vessel 5 and an absence of the liquid sample in the reaction vessel 5 is present.

A series of steps performed by the stirring control unit 21 for the abnormal determination described above will be explained below with reference to a flowchart. First, the stirring control unit 21 detects initial frequency characteristics of the reference reflected power WI of the surface acoustic wave element 27 before the self-heating (step S102). For the initial frequency characteristics, after the stirring apparatus 20 is mounted to the automatic analyzer 1 or after the stirring apparatus 20 itself is assembled, a reflected power reflected by and returning from the transducer 27b is detected by the detecting circuit 26 while the driving frequency of the surface acoustic wave element 27 is changed, and is output to the determining unit 23a to be stored therein as reflected power data.

Next, the stirring control unit 21 detects the in-operation reflected power which is reflected from the surface acoustic wave element 27 in stirring the liquid sample kept in the reaction vessel 5 by the detecting circuit 26 (step S104). The in-operation reflected power detected by the detecting circuit 26 is output to and stored in the determining unit 23a as reflected power data. Here, in contrast to the detection of the initial frequency characteristics which is an operation performed right after the assembly of the automatic analyzer 1 and the stirring apparatus 20, the detection of the in-operation reflected power is an operation to be performed in actually analyzing the specimen by using the automatic analyzer 1 and the stirring apparatus 20. The stirring control unit 21 then calculates the difference between the in-operation reflected power and the reference reflected power WI at the same driving frequency (step S106). The difference between the in-operation reflected power and the reference reflected power WI is calculated by the determining unit 23a based on the stored reflected power data.

Thereafter, the stirring control unit 21 determines whether the difference between the in-operation reflected power and the reference reflected power WI exceeds the threshold value T by the determining unit 23a (step S108). When the difference between the in-operation reflected power and the reference reflected power WI exceeds the threshold value T ("Yes" at step S108) as a result of the determination, the determining unit 23a determines a presence of an abnormality (step S110). In this case, the determining unit 23a outputs the effect to the control unit 15, makes the effect displayed on the display unit 17 via the control unit 15, and makes the operation of the automatic analyzer 1 stop via the control unit 15.

On the other hand, when the difference between the in-operation reflected power and the reference reflected power WI does not exceed the threshold value T ("No" at step S108) as a result of the determination, the determining unit 23a does not determine a presence of an abnormality and goes back to step S104, and the stirring control unit 21 detects an in-operation reflected power for a subsequent new specimen. By repeating the steps described above, the stirring apparatus 20 can easily determine a presence of an abnormality such as a detachment of the surface acoustic wave element 27 from the reaction vessel 5 and an absence of the liquid sample in the reaction vessel 5.

It should be noted that, though a case of using two reagent tables is explained in the automatic analyzer 1, the number of the reagent table may be one. Besides, the automatic analyzer according to the present invention may be configured, by taking the automatic analyzer 1 as one unit, to have a plurality of units in combination.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A stirring apparatus, comprising:
    an acoustic wave generating unit that is provided in a vessel keeping a liquid and generates an acoustic wave toward the liquid, the liquid being stirred by the acoustic wave;
    a driving unit that drives the acoustic wave generating unit;
    a detecting unit that detects a reflected power reflected from the acoustic wave generating unit; and
    a determining unit that determines a presence of an abnormality based on the reflected power detected by the detecting unit, wherein
    the determining unit determines the presence of the abnormality when a difference between an in-operation reflected power which is reflected from, during an operation, the acoustic wave generating unit and a reference reflected power of the acoustic wave generating unit at a same driving frequency exceeds a predetermined value.

2. The stirring apparatus according to claim 1, wherein the acoustic wave generating unit is a surface acoustic wave element.

3. An analyzer which stirs a plurality of different liquids to cause a reaction and analyzes a reaction liquid, wherein the analyzer analyzes the reaction liquid by using the stirring apparatus according to claim 1 to stir and react the plurality of different liquids.

4. An abnormality determining method for a stirring apparatus which includes an acoustic wave generating unit that is provided in a vessel keeping a liquid and generates an acoustic wave toward the liquid, and a driving unit that drives the acoustic wave generating unit, and stirs the liquid by the acoustic wave, the abnormality determining method comprising:
    detecting an initial frequency characteristic of a reference reflected power of the acoustic wave generating unit;
    detecting an in-operation reflected power reflected from, during an operation, the acoustic wave generating unit; and
    calculating a difference between the in-operation reflected power and the reference reflected power at a same driving frequency, and determining a presence of an abnormality when the difference exceeds a predetermined value.

5. The abnormality determining method of the stirring apparatus according to claim 4, wherein the acoustic wave generating unit is a surface acoustic wave element.

* * * * *